(12) United States Patent
Anderson (10) Patent No.: US 12,011,153 B2
(45) Date of Patent: Jun. 18, 2024

(54) ELASTIC INTRODUCER SHEATH

(71) Applicant: Medtronic Vascular, Inc., Santa Rosa, CA (US)

(72) Inventor: Marc Anderson, Galway (IE)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 0 days.

(21) Appl. No.: 17/669,784

(22) Filed: Feb. 11, 2022

(65) Prior Publication Data

US 2022/0160344 A1  May 26, 2022

Related U.S. Application Data

(60) Continuation of application No. 16/680,033, filed on Nov. 11, 2019, now Pat. No. 11,246,581, which is a
(Continued)

(51) Int. Cl.
*A61B 17/02* (2006.01)
*A61F 2/24* (2006.01)
(Continued)

(52) U.S. Cl.
CPC ........ *A61B 17/0218* (2013.01); *A61F 2/2436* (2013.01); *A61M 25/0023* (2013.01);
(Continued)

(58) Field of Classification Search
CPC ....... A61B 2017/0225; A61B 17/0218; A61M 29/00; A61M 29/02
See application file for complete search history.

(56) References Cited

U.S. PATENT DOCUMENTS 5,573,517 A   11/1996   Bonutti et al.
5,935,122 A   8/1999    Fourkas et al.
(Continued)

FOREIGN PATENT DOCUMENTS

| CN | 2245986 | 1/2017 |
|----|---------|--------|
| EP | 2070560 | 6/2009 |
| EP | 2179762 | 4/2010 |

OTHER PUBLICATIONS

International Search Report and Written Opinion for related International Application No. PCT/US2018/026850 dated Jul. 12, 2018 (16 pages).

*Primary Examiner* — Julianna N Harvey
(74) *Attorney, Agent, or Firm* — Wentsler LLC (57) ABSTRACT

An introducer sheath system including an outer layer, an inner layer, and a dilator is disclosed. The outer layer is circumferentially extending between a first longitudinal edge and a second longitudinal edge. An expandable gap is defined between the first and second longitudinal edges. The inner layer is disposed within the outer layer. The inner layer is configured to be continuously circumferentially expandable. The inner layer includes a non-extended state having a circumferential portion extending circumferentially inside the outer layer and a fold portion extending into an interior cavity of the inner layer. The inner layer includes an extended state wherein the fold portion extends at least partially circumferentially between the first and second longitudinal edges. The dilator is extendable longitudinally within the inner layer. The dilator includes a recess configured to accommodate the fold portion of the inner layer.

20 Claims, 5 Drawing Sheets

Related U.S. Application Data division of application No. 15/495,657, filed on Apr. 24, 2017, now Pat. No. 10,499,895.

(51) Int. Cl.
*A61M 25/00* (2006.01)
*A61M 25/06* (2006.01)
*A61M 29/00* (2006.01)

(52) U.S. Cl.
CPC ........ *A61M 25/0662* (2013.01); *A61M 29/00* (2013.01); *A61B 2017/0225* (2013.01); *A61B 2017/0237* (2013.01); *A61M 2025/0024* (2013.01); *A61M 25/005* (2013.01)

(56) References Cited

U.S. PATENT DOCUMENTS

| | | | |
|---|---|---|---|
| 5,944,691 A | 8/1999 | Querns et al. | |
| 5,997,508 A | 12/1999 | Lunn et al. | |
| 6,090,072 A | 7/2000 | Kratoska et al. | |
| 6,183,443 B1 | 2/2001 | Kratoska et al. | |
| 7,713,193 B2 * | 5/2010 | Nance | A61B 17/3439 600/184 |
| 7,927,309 B2 | 4/2011 | Palm | |
| 10,548,631 B2 | 2/2020 | Fitterer et al. | |
| 2003/0065353 A1 | 4/2003 | Horzewski et al. | |
| 2004/0087968 A1 | 5/2004 | Core | |
| 2008/0015625 A1 * | 1/2008 | Ventura | A61N 1/056 606/191 |
| 2009/0209969 A1 | 8/2009 | Wolfe | |
| 2009/0240202 A1 | 9/2009 | Drasler et al. | |
| 2010/0094392 A1 * | 4/2010 | Nguyen | A61M 25/0023 623/1.11 |
| 2012/0095448 A1 | 4/2012 | Kajii | |
| 2013/0079872 A1 | 3/2013 | Gallagher | |
| 2013/0331639 A1 | 12/2013 | Campbell et al. | |
| 2014/0121629 A1 * | 5/2014 | Macaulay | A61M 25/005 604/524 |
| 2014/0236122 A1 | 8/2014 | Anderson et al. | |
| 2014/0236123 A1 * | 8/2014 | Birmingham | A61M 25/0012 604/524 |
| 2015/0238178 A1 * | 8/2015 | Carroux | A61B 1/307 600/208 |
| 2017/0014157 A1 | 1/2017 | Coyle et al. | |
| 2018/0303610 A1 | 10/2018 | Anderson | |
| 2020/0077998 A1 | 3/2020 | Anderson | |

* cited by examiner

ELASTIC INTRODUCER SHEATH

CROSS-REFERENCE TO RELATED APPLICATION

This application is a Continuation of U.S. patent application Ser. No. 16/680,033, filed Nov. 11, 2019, entitled "ELASTIC INTRODUCER SHEATH," now allowed, which is a Divisional of U.S. patent application Ser. No. 15/495,657, filed Apr. 24, 2017, entitled, "ELASTIC INTRODUCER SHEATH," now U.S. Pat. No. 10,499,895, the entire teachings of which are incorporated herein by reference.

BACKGROUND

A variety of diagnostic and therapeutic procedures involve the introduction of a device through a natural or artificially created access pathway. A general objective of access systems, which have been developed for this purpose, is to minimize the cross-sectional area of the puncture and pathway, while maximizing the available space for the diagnostic or therapeutic instrument.

A percutaneous introducer sheath can be used to access the vascular system of a patient to introduce and position various transcatheter medical devices within the patient. The introducer sheath is a tube-like member which is partially inserted into the vasculature at a puncture site while the proximal, or working end, of the introducer sheath remains outside of the vasculature for accessibility to introduce a transcatheter medical device through the sheath. A guide wire can be inserted through the introducer sheath and subsequently steered through the vascular system to the site of therapy.

Large-profile transcatheter medical devices have traditionally required a larger-profile introducer sheath which provides a fixed internal clearance to allow the device to pass through the patient's vasculature. Such procedures using the large-profile transcatheter medical devices, typically through the femoral artery, are therefore limited to patients with sufficient vessel size to accommodate the introducer sheath. In order to extend the availability of large-profile transcatheter devices to patients with smaller vessel sizes, an introducer with a smaller profile that locally expands within the patient's vasculature to allow passage of the large-profile transcatheter device is desired.

SUMMARY

One aspect of the present disclosure relates to an introducer sheath system including an outer layer, an inner layer, and a dilator. The outer layer is circumferentially extending between a first longitudinal edge and a second longitudinal edge. An expandable gap is defined between the first and second longitudinal edges. The inner layer is disposed within the outer layer. The inner layer is configured to be continuously circumferentially expandable. The inner layer includes a non-extended state having a circumferential portion extending circumferentially inside the outer layer and a fold portion extending into an interior cavity of the inner layer. The inner layer includes an extended state wherein the fold portion extends at least partially circumferentially between the first and second longitudinal edges. The dilator is extendable longitudinally within the inner layer. The dilator includes a recess configured to accommodate the fold portion of the inner layer.

Another aspect of the present disclosure relates to an elastic surgical access system including an outer sheath, an inner sheath, and a dilator. The outer sheath includes a circumferentially non-continuous layer extending between a first longitudinal edge and a second longitudinal edge. The first and second longitudinal edge are non-overlapping. The inner sheath is attached within the outer layer and is circumferentially continuous. The inner sheath includes a circumferential portion extending circumferentially within the outer layer and a fold portion extendable within an interior lumen of the inner sheath. The fold portion is longitudinally aligned between the first and second longitudinal edges. The dilator is insertable into the interior lumen of the inner sheath. The dilator includes a recessed channel configured to accommodate the fold portion.

Another aspect of the present disclosure relates to an introducer sheath system an outer sheath, an inner sheath disposed within the outer sheath, and a dilator insertably extendable within the inner sheath. The outer sheath includes a circumferentially discontinuous layer and an elastic frame. The outer sheath is discontinuous between a first longitudinal edge and a second longitudinal edge. The first and second longitudinal edges abut in a non-expanded state and a gap is formed between the first and second longitudinal edges in an expanded state. The inner sheath is comprised of a circumferentially continuous membrane including a circumferential portion attached to the outer sheath and a fold portion freely extendable into an interior lumen of the inner sheath in the non-expanded state and circumferentially aligned with the circumferential portion in the extended state. The dilator includes a recessed channel configured to accommodate the fold portion. The dilator is configured to transition the outer and inner sheaths from the non-expanded state to the expanded state.

DETAILED DESCRIPTION

Figure 1:
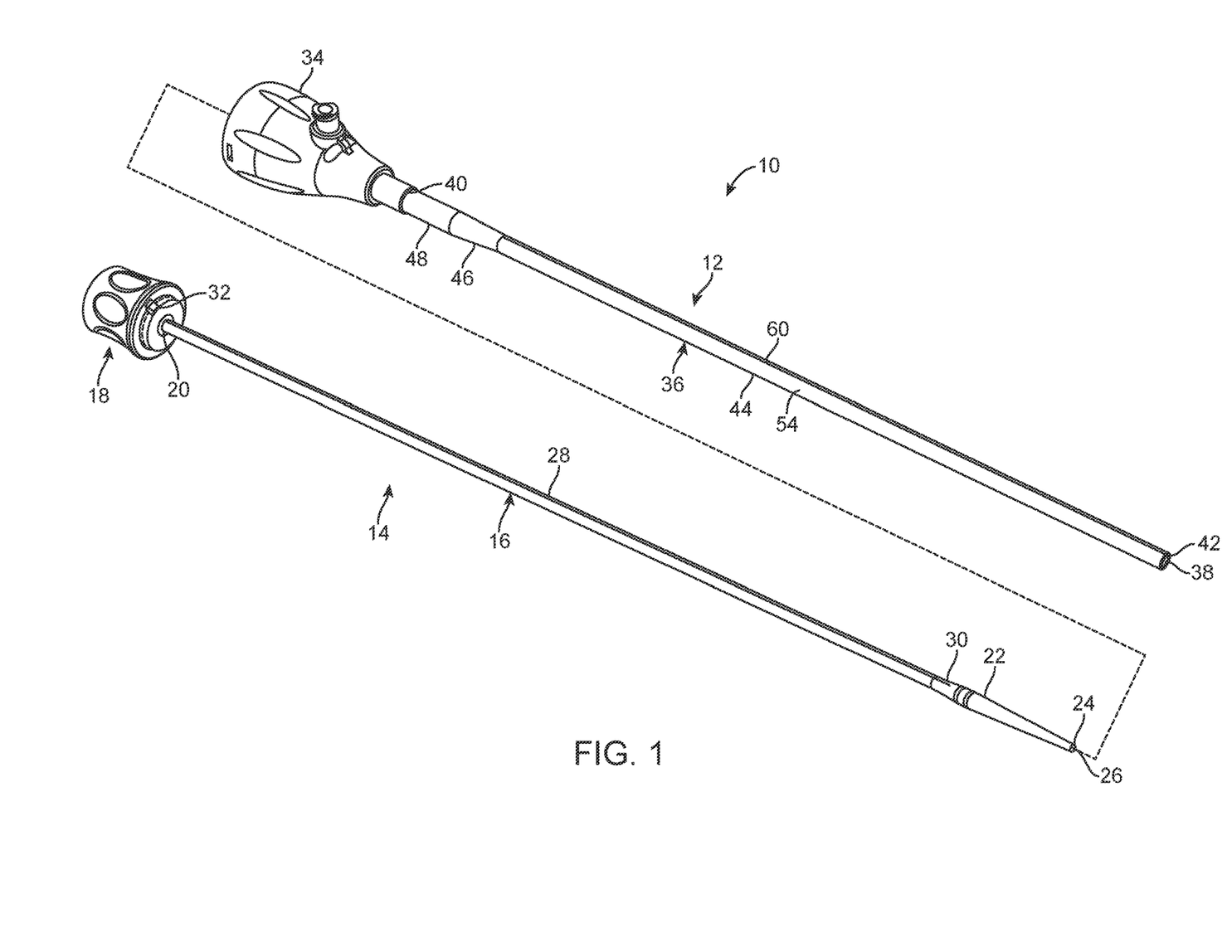
FIG. 1 is a perspective view of an introducer sheath system including an introducer sheath and a dilator in accordance with an embodiment of the present disclosure.

FIG. 1 illustrates an introducer sheath system 10 including an introducer sheath 12 and a dilator 14 in accordance with aspects of the present disclosure. The introducer sheath 12 is illustrated with the dilator 14 separately disposed in FIG. 1 for clarity. The dilator 14 is insertable into the introducer sheath 12, as described further below. The introducer sheath system 10 can be sized for a transcatheter heart valve procedure and can be used with a transcatheter heart valves and delivery system, for example.

Figure 2:
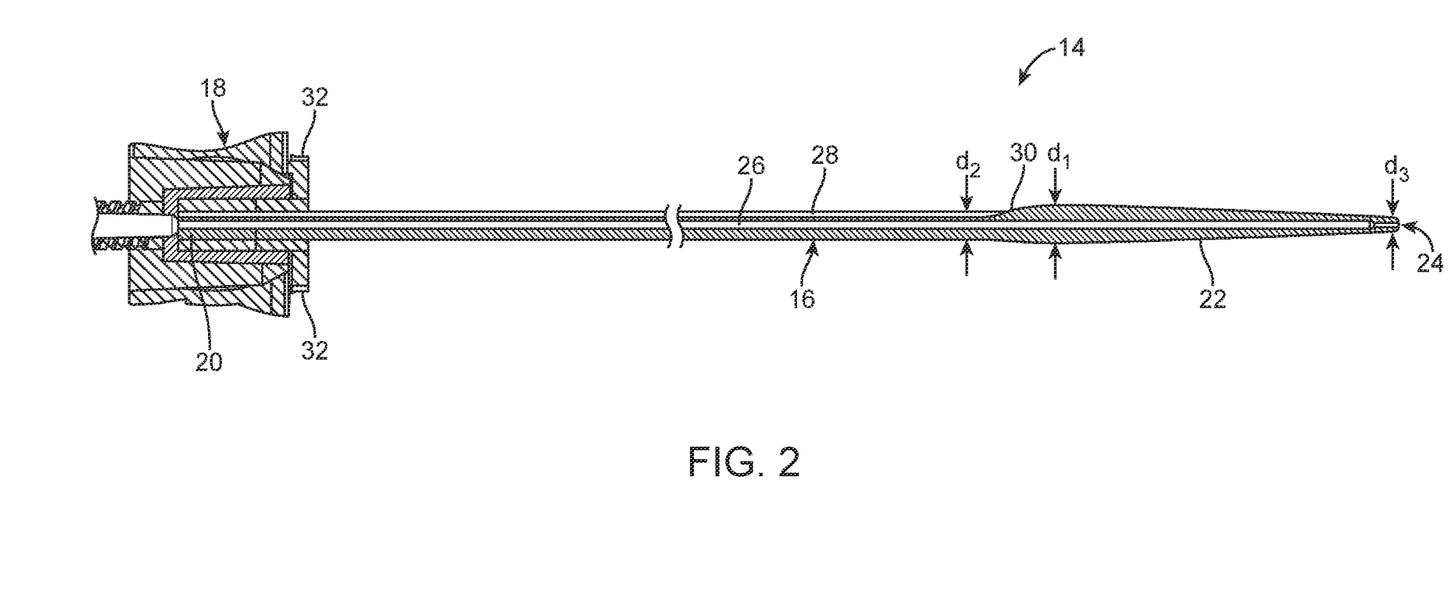
FIG. 2 is a cross-sectional view of the dilator of FIG. 1 in accordance with aspects of the present disclosure.

With additional reference to the cross-sectional view of FIG. 2, the dilator 14 includes an elongated tubular body 16 coupled to a hub 18 at a proximal end 20 of the elongated tubular body 16. The elongated tubular body 16 includes a dilator tip 22 disposed at the distal end 24. The dilator tip 22 can have a conical shape and taper from a diameter $d_1$ that is slightly greater than a diameter $d_2$ of the elongated tubular body 16 to a diameter $d_3$ smaller than the elongated tubular body 16 to ease insertion into the introducer sheath 12 and into the patient's vessel. The dilator 14 includes an axial lumen 26 extending along a central longitudinal axis 27 throughout the length of the dilator 14, fluidly open from the distal end 24 and through the hub 18, for insertion of a guidewire. The axial lumen 26 can have a larger diameter within the hub 18 than at the distal end 24 to facilitate ease of insertion of the guidewire (not shown) and to support axial strength of the elongated tubular body 16. In one embodiment, at least the elongated tubular body 16 of the dilator 14 is a high-density polyethylene (HDPE)/low-density polyethylene (LDPE) blend.

The dilator 14 includes a recessed channel 28 extending along the elongated tubular body 16. The recessed channel 28 can extend between a proximal portion 30 of the dilator tip 22 to the proximal end 20 of the elongated tubular body 16. The recessed channel 28 is openingly exposed along an exterior surface of the elongated tubular body 16.

The hub 18 of dilator 14 can include one or more alignment nubs 32 correspondingly mateable with one or more alignment notches (not shown) of the introducer sheath 12. The alignment nub 32 can provide for coupling of the dilator 14 with the introducer sheath 12. The alignment nub 32 can provide for a longitudinal alignment of the dilator 14 within the introducer sheath 12. The mateable alignment connection of the dilator 14 within the introducer sheath 12 can be a snap-type connection, for example, or other suitable connection that does not require axial twisting or turning of the introducer sheath 12 and the dilator 14 relative to one another during assembly. The alignment nub 32 and notch, or other suitable connection, provides a single alignment orientation and assembly of the introducer sheath system 10.

With continued reference to FIG. 1, the introducer sheath 12 includes a hub 34 for connection with the hub 18 of the dilator and to syringes and other peripheral devices. The introducer sheath 12 includes an elastic sheath body 36 that is an elongated tubular body having a lumen 38 for introduction of the dilator 14 and transcatheter medical devices. The elastic sheath body 36 has a proximal end 40 coupled to the hub 34 and a distal end 42 insertable into the vasculature of a patient. In one embodiment, the distal end 42 includes a tapered tip for insertion through the vessel wall without roll back of the tip. The elastic sheath body 36 includes an expandable section 44 extending from the distal end 42 and a transition section 46. The transition section 46 tapers the diameter of the elastic sheath body 36 from a full diameter section 48 to expandable section 44. The transition section 22 facilitates a smooth transition from the hub 34 and the full diameter section 48 to the expandable section 46. The full diameter section 48 and the transition section 46 are circumferentially continuous and concentric. The expandable section 44 is circumferentially expandable along a length to allow for local expansion and subsequent recoil to reduce trauma to a patient's vessel, as described further below.

Figure 3:
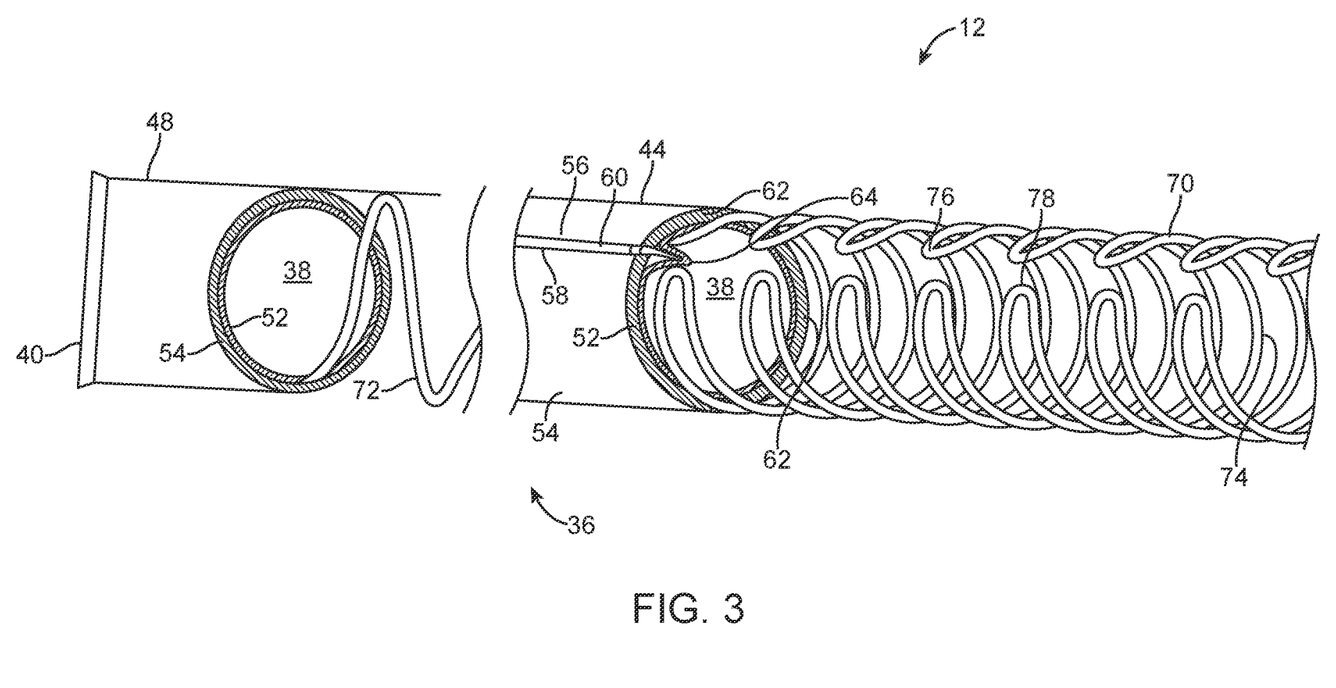
FIG. 3 is a partial perspective and cut away view of an introducer sheath in accordance with an embodiment of the present disclosure.
Figure 4A:
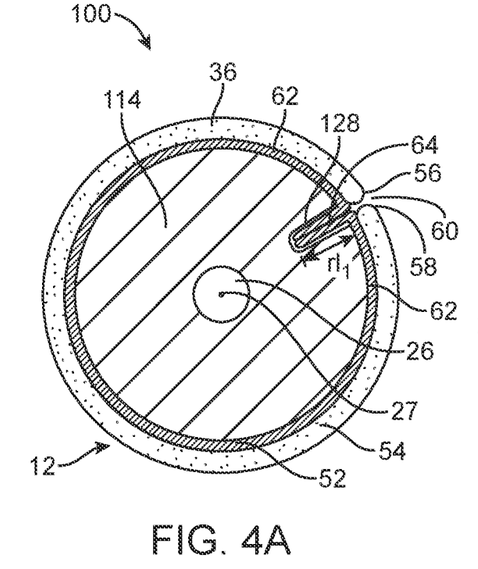
FIG. 4A is an enlarged cross-sectional view of an introducer sheath system in a non-expanded state with an example dilator inserted in accordance with an embodiment of the present disclosure.
Figure 4B:
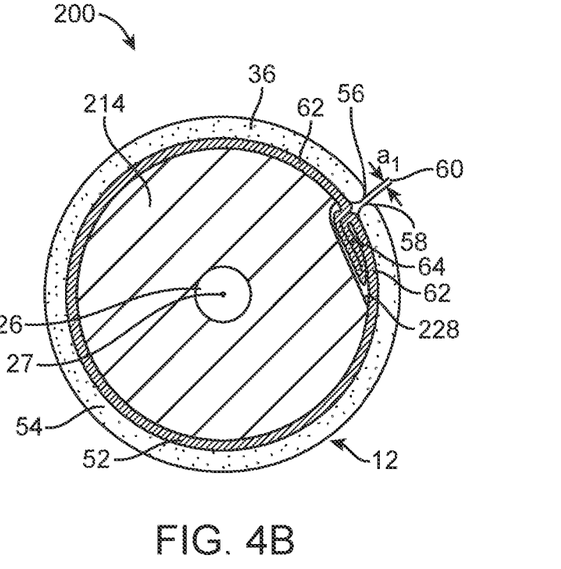
FIG. 4B is an enlarged cross-sectional view of an introducer sheath system in a non-expanded state with another example dilator inserted in accordance with an embodiment of the present disclosure.

FIG. 3 is a perspective partial cut away view of the full diameter section 48 and the expandable section 44 of the introducer sheath 12 according to one example embodiment. The introducer sheath 12 includes an inner layer 52 and an outer layer 54. As further illustrated in FIG. 3, outer layer 54 circumferentially extends between a first longitudinal edge 56 extending in an axial direction of the introducer sheath 12 and a second longitudinal edge 58 extending in the axial direction of the introducer sheath 12. An expandable gap 60 is defined between first and second longitudinal edges 56, 58. In some embodiments, the first and second longitudinal edges 56, 58 abut one another when the sheath is in a non-expanded state. The first longitudinal edge 56 and second longitudinal edge 58 do not circumferentially overlap in a non-expanded state and the outer circumference of the elastic sheath body 36 is symmetric. As illustrated in FIGS. 3, 4A, and 4B, the first longitudinal edge 56 circumferentially faces the second longitudinal edge 58 in a non-expanded state, and the first longitudinal edge 56 comprises an unobstructed circumferential view of the second longitudinal edge 58 in the non-expanded state. The inner layer 52 is disposed within the outer layer 54. The inner layer 52 is continuously circumferentially expandable and forms an interior surface of the expandable lumen 38. The inner layer 52 of the expandable section 44 includes a circumferential portion 62 that is circumferentially disposed along an interior surface of the outer layer 54 and a fold portion 64 that is extendable into an interior cavity, or the lumen 38. As will be appreciated by FIGS. 3, 4A and 4B, the fold portion 64 extends in the axial direction of the introducer sheath 12 along the first longitudinal edge 56 and the second longitudinal edge 58. In one embodiment, the circumferential portion 62 is adhered or otherwise attached to the outer layer 54 and the fold portion 64 extends from the circumferential portion 62 unattached, or free disposed, within the outer layer 54. In one embodiment, the circumferential portion 62 is fully adhered to the outer layer 54 from the proximal end 40 to the distal end 42 of the elastic sheath body 36.

A wire structure 70 can be included in the elastic sheath body 36 to provide kink resistance for the introducer sheath 12 and also allow the introducer sheath 12 to elastically and actively recoil to a reduced diameter after passage of a transcatheter medical device through the expandable section 44 of the elastic sheath body 36. The wire structure 70 can laminated between the inner layer 52 and the outer layer 54 or embedded within the outer layer 54. The wire structure 70 includes at least one repeating longitudinal pattern. For example, the wire structure 70 can include a sinusoid pattern, a square pattern, a modified square pattern, or any other suitable repeating pattern. In full diameter section 48, the wire structure 70 is coiled, for example. In full diameter section 70, both the inner layer 52 and the outer layer 54 are circumferentially continuous and concentric with a coiled wire structure 72. The outer layer 54 and a shaped wire structure 74 are not circumferentially continuous in the expandable section 44 and form the longitudinal gap 60 between the first and second longitudinal edges 56, 58. In one embodiment, the expandable section 44 includes the inner layer 52 circumferentially continuous and the outer layer 54 circumferentially discontinuous at the first and second longitudinal edges 56, 58 with the wire structure 70 bent around a central longitudinal axis into the wire structure 74 that is C-shaped to form an elastic frame of a series of non-continuous circumferential loops that do not overlap longitudinally across the gap 60. In one embodiment, when the elastic sheath body 36 is in a non-expanded, or collapsed, configuration, the first loop portions 76 are positioned circumferentially adjacent to the second loop portions 78 on opposite sides of the gap 60. The elastic frame formed by the wire structure 70 is biased to bring the first longitudinal edge 56 and the second longitudinal edge 58 of the outer layer 54 proximal to each other.

FIGS. 4A and 4B are enlarged lateral cross-sectional views of assembled introducer sheath systems 100, 200 including example dilators 114, 214 in accordance with embodiments of the present disclosure. The assembled introducer sheath systems 100, 200 are similar to the introducer sheath system 10 and include the introducer sheath 12. The cross-sectional views are through the expandable section 44 of the introducer sheath 12 in a non-expanded state. As described above, the elastic sheath body 36 includes the outer layer 54 and the inner layer 52. Although not shown, the wire structure 70 can also be included as part of the outer layer 54. The inner layer 52 includes the circumferential portion 62 and the fold portion 64. The outer surface of the circumferential portion 62 is attached to the inner surface of the outer layer 54. The fold portion 64 is disposed unattached to the outer layer 54 between the first and second longitudinal edges 56, 58, to be extendable across the expandable gap 60.

In some embodiments, elongated tubular bodies 116, 216 of the dilators 114, 214 have an outer diameter that is substantially equivalent to an inner diameter of the expandable section 44 in the non-expanded state. Recessed channels 128, 228 of the dilators 114, 214 are configured to accommodate the fold portion 64 of the inner layer 52. The shape and configuration of the fold portion 64 and recessed channels 128, 228 of the dilators 114, 214 are exemplary and are not meant to be limiting. The gap 60 of the outer layer 54 is radially aligned with the recessed channel 128, 228 such that the fold portion 64 is extendable within the recessed channel 128, 228 of the dilator 114, 214. In some embodiments, the fold portion 64 configured as a single fold of two parallel layers and then either extends radially into the recess 128 or is further folded toward, or against, the circumferential portion 62 to extend within recess 228. With reference to FIG. 4A, the recessed channel 128 extends radially from an exterior surface of the dilator 114 and into a thickness of the dilator 114 toward the central longitudinal axis 27. In one embodiment, the recessed channel has a radially length $rl_1$ of approximately 2 mm and is sized to accommodate the fold portion 64 of the inner layer 52 having an unfolded arc length of approximately 4 mm. With reference to FIG. 4B, the recessed channel 228 the recess can be L-shaped or generally follow the shape of the outer circumference of the introducer with an indented area along a portion of the exterior surface and aligned with the longitudinal gap. The fold portion 64 is movable into and out of the recessed channel 128, 228 of the dilator 114, 214 in response to longitudinal movement of the dilator and/or a transcatheter medical device through the expandable section 44 and increased internal circumferential accommodations necessitated by the passage of such within the expandable section 44, as discussed further below.

Figure 4C:
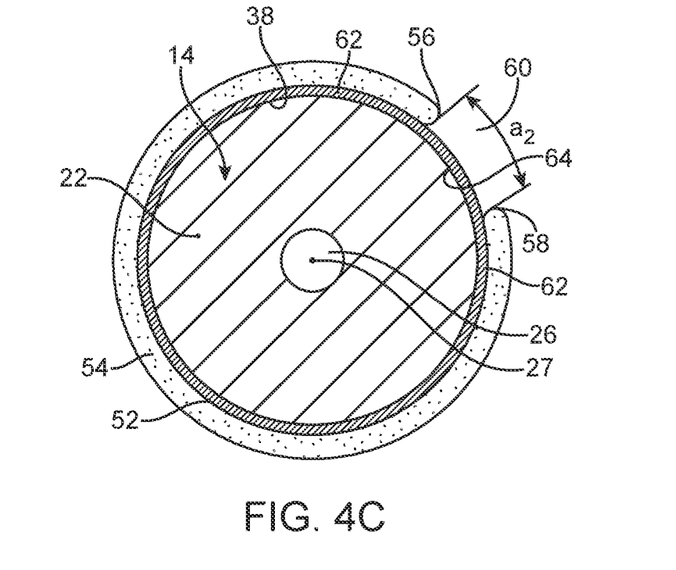
FIG. 4C is an enlarged cross-sectional view of an introducer sheath system in an expanded state in accordance with an embodiment of the present disclosure.

FIG. 4C illustrates the expandable section 44 in an expanded state and includes a longitudinal gap 60 visible in an expanded configuration. As illustrated in FIG. 4C, the inner layer 52 has an extended state wherein the fold portion 54 extends across the expandable gap 60 between the first and second longitudinal edges 56, 58. As seen in a comparison of FIGS. 4A-4B and FIG. 4C, the gap 60 has a first arc length $a_1$ in the non-expanded state and a second arc length $a_2$ in the expanded state, with the first arc length $a_1$ being less than the second arc length $a_2$. The inner layer 52 is circumferentially continuous and forms the lumen 38, through which the dilator tip 22 of the dilator 14 and transcatheter medical devices can extend within. In the expanded state, the first and second longitudinal edges 56, 58 of the outer layer 54 are separated by the expanded gap 60 and the outer layer 54 being circumferentially discontinuous. As illustrated, the circumferential width, or arc length, of the expandable gap 60 can be temporarily increased to accommodate passage of a device or the dilator 14. The inner layer 52 maintains the circumferentially continuous lumen 38 between the proximal and distal ends 40, 42 of the elastic sheath body 36 in both the non-expanded and expanded states.

In one embodiment, the inner layer 52 is a circumferentially continuous biocompatible material layer such as a tetrafluoroethylene (TFE), for example. In alternate embodiments, the inner layer can be Teflon®, polytetrafluoroethylene (PTFE), polyethylene, polyethylene terephthalate (PET), or polyester. The inner layer 52 can have a low coefficient of friction on its inner surface to facilitate advancement of a transcatheter medical device through the elastic sheath body 36. The inner layer 52 can have a material thickness that is less than a material thickness of the outer layer 54. In one embodiment, the outer layer 54 is a biocompatible material layer such as polyurethane (e.g. Pellethane®, Elasthane™, Texin®, or Tecothane®) and can include 20% barium sulfate added as a radipacifier. In alternate embodiments, the outer layer 54 can be a polyamide polyether block copolymer such as Pebax®, nylon 12, or polyethylene. The material for the outer layer 54 can also be loaded with tungsten or bismuth subcarbonate to add radiopacity so that the elongated sheath body 36 can be radio detectable (radiopaque). The wire structure 70 can be nickel titanium, Nitinol, with the diameter of the wire ranging from approximately 0.005 inches to approximately 0.02 inches. In alternate embodiments, the wire structure 70 can be nickel-cobalt-chromium-molybdenum (MP35N), stainless steel, high spring temper steel, or any other metal or composite having elastic properties to permit extension and recoil of the introducer sheath 12.

Figure 5:
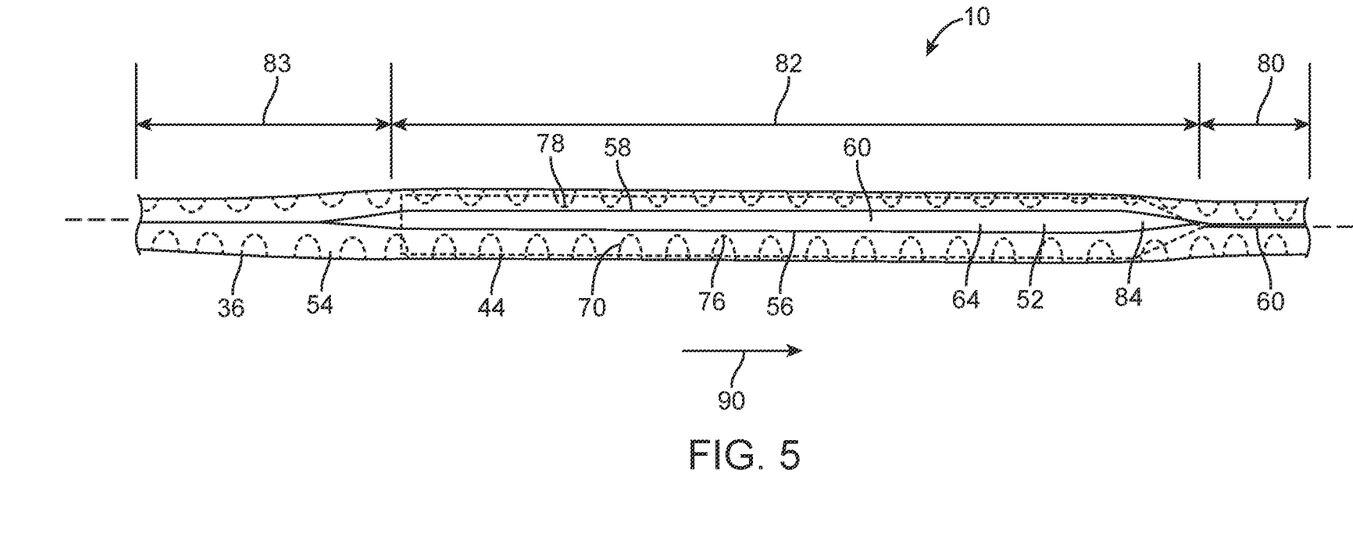
FIG. 5 is a top view of an introducer sheath system in accordance with an embodiment of the present disclosure.

As further illustrated in FIG. 5, the introducer sheath system 10 is designed to allow for local circumferential expansion and subsequent recoil to reduce trauma to a patient's vessel. Local expansion and subsequent recoil of the elastic sheath body 36 profile can be less traumatic on the patient's vessel than a sustained expansion for a large-profile introducer sheath system. Typically, the introducer sheath system 10 is inserted into a vessel, such as the femoral artery, passing through the skin of a patient, such that the distal end 42 of the introducer sheath and the distal end 24 of the dilator 14 are jointly inserted into the vessel. While introducing a transcatheter device 84, the elastic sheath body 36 can transition from the collapsed, or non-expanded state 80 prior to accommodating the transcatheter device 84, the expanded state 82 to accommodate the transcatheter device 84, and a reduced state 83 after passage of the transcatheter device 84. The diameter of the elastic sheath body 36 increases in the expanded state 80 to accommodate the transcatheter device 84. This increase in diameter is accomplished by the first loop portions 76 and the second loop portions 78 of the wire structure 70 and the first longitudinal edge 56 and the second longitudinal edge 58 of the outer layer 54 diverging circumferentially to increase the effective diameter of the elastic sheath body 36. As the elastic sheath body 36 increases in diameter, the fold portion 64 of the inner layer 52 is pulled, or forced, out of the recessed channel 28 of the dilator 14 and flattened, or circumferentially extended, to allow the inner fold portion 64 to span across the gap 60. Thus, the fold portion 64 of the inner layer 52 extends across the gap 60 and maintains a circumferentially continuous structure.

An arrow 90 shows the direction of travel of the transcatheter device 84 through introducer sheath system 10. The expanded state 82 of the elastic sheath body 36 is limited to the portion of the expandable section 44 that surrounds the transcatheter device 84. As the transcatheter device 84 is moved distally in the direction of the arrow 90, distal portions of the expandable section 44 transition to the expanded state 82 to accommodate the transcatheter device 84. Furthermore, the proximal portions of the expandable section 44 transition to the reduced state 83 following passage of the transcatheter device 84. The reduced state 83 can have a diameter equivalent, or slightly larger, than that of the non-expanded state 82.

After passage of the transcatheter device 84, elastic sheath body 36 recoils and reduces in diameter to non-expanded state 80, proximal to the transcatheter device 84. The recoil and reduction in diameter is accomplished by the elasticity of the wire structure 70. The elasticity of the wire structure 70 allows the first loop portions 76 and the second loop portions 78 of the wire structure 70 and the first longitudinal edge 56 and the second longitudinal edge 58 of the outer layer 54 to converge circumferentially and to reduce the effective diameter of the elastic sheath body 36. The fold portion 64 can have a "memory" and transitions back into a folded configuration as the elastic sheath body 36 reduces in diameter. The recessed channel 28 is again utilized to accommodate the fold portion 64 of the inner layer 52 and the gap 60 width, or arc length, is diminished with the first longitudinal edge 56 and the second longitudinal edge 58 resuming positions adjacently disposed across the gap 60 and in some cases abutting each other.

With returning reference to the introducer sheath assembly of FIG. 1, in one embodiment, the introducer sheath assembly 10 is factory assembled with the dilator 14 fully inserted and coupled with the introducer sheath 12. The gap 60 of the elastic sheath body 36 and the recessed channel 28 of the dilator 14 are radially aligned and the fold portion 64 of the inner layer 52 is aligned and inserted within the recessed channel 28 of the dilator 14. In one embodiment, the fold portion 64 can be longitudinally slidably inserted into the recessed channel 28 as the dilator 14 is slidably assembled into the introducer sheath 12. In another embodiment, the fold portion 64 is inserted into the recessed channel 28 after assembly of the dilator 14 and introducer sheath 12 with an exterior force. The alignment notches (not shown) of the hub 34 of the introducer sheath 12 and the alignment nubs 32 of the hub 18 of the dilator 14 are mateably coupled to maintain the dilator 14 alignment and retention within the introducer sheath 12. In one embodiment, the coupling would be maintained under normal operating forces but can be manually released and de-coupled with sufficient applied force.

Although the present disclosure has been described with reference to preferred embodiments, workers skilled in the art will recognize that changes can be made in form and detail without departing from the spirit and scope of the present disclosure.

What is claimed is:

1. An introducer sheath system comprising:
   an outer layer circumferentially extending between a first longitudinal edge extending in an axial direction of the introducer sheath system and a second longitudinal edge extending in the axial direction, wherein the first longitudinal edge circumferentially faces the second longitudinal edge in a non-expanded state, the first longitudinal edge comprises an unobstructed circumferential view of the second longitudinal edge in the non-expanded state, and a circumferential gap is defined between the first longitudinal edge and the second longitudinal edge in an expanded state; and
   an inner layer disposed within the outer layer, the inner layer configured to be continuously circumferentially expandable from the non-expanded state to the expanded state, the inner layer comprising a circumferential portion extending circumferentially inside the outer layer and a fold portion extending in the axial direction adjacent the first longitudinal edge and the second longitudinal edge in the non-expanded state, and the fold portion is configured to at least partially unfold to at least partially circumferentially extend across the circumferential gap between the first longitudinal edge and second longitudinal edge in the expanded state.

2. The introducer sheath system of claim 1, further comprising a dilator positioned within the inner layer.

3. The introducer sheath system of claim 2, further comprising an axial lumen extending along a central longitudinal axis throughout a length of the dilator.

4. The introducer sheath system of claim 2, wherein the fold portion is configured to extend within a recessed channel of the dilator in the non-expanded state.

5. The introducer sheath system of claim 4, wherein the recessed channel extends radially inward from an exterior surface of the dilator toward a central longitudinal axis of the dilator.

6. The introducer sheath system of claim 4, wherein the recessed channel is L-shaped.

7. The introducer sheath system of claim 4, wherein the dilator comprises a body comprising an axial lumen and the recessed channel is separated from the axial lumen by a body of the dilator.

8. The introducer sheath system of claim 1, further comprising a wire structure.

9. The introducer sheath system of claim 8, wherein the wire structure comprises at least one repeating longitudinal pattern.

10. The introducer sheath system of claim 8, wherein the wire structure is elastic.

11. The introducer sheath system of claim 1, wherein an outer surface of the circumferential portion of the inner layer is attached to an inner surface of the outer layer.

12. The introducer sheath system of claim 1, wherein the fold portion is a single fold in the non-expanded state.

13. The introducer sheath system of claim 12, wherein the single fold extends radially inwardly from the first longitudinal edge and the second longitudinal edge in the non-expanded state.

14. The introducer sheath system of claim 1, wherein the inner layer has a thickness that is less than a thickness of the outer layer.

15. The introducer sheath system of claim 1, wherein the outer layer comprises a radiopaque material.

16. The introducer sheath system of claim 1, wherein the outer layer is symmetrical in the non-expanded state.

17. The introducer sheath system of claim 1, wherein the outer layer is elastic.

18. The introducer sheath system of claim 1, wherein the fold portion comprises two layers comprising facing inner surfaces that engage one another, and the two layers are further folded over the circumferential portion such that an outer surface of one of the two layers engages an outer surface of the circumferential portion.

19. The introducer sheath system of claim 1, wherein the first longitudinal edge and the second longitudinal edge are non-overlapping in the non-expanded state.

20. The introducer sheath system of claim 1, wherein the circumferential gap is further defined between the first longitudinal edge and the second longitudinal edge in the non-expanded state.

\* \* \* \* \*